United States Patent [19]

Parker

[11] Patent Number: 5,770,624
[45] Date of Patent: Jun. 23, 1998

[54] CERTAIN ALPHA-SUBSTITUTED ARYLSULFONAMIDO ACETOHYDROXAMIC ACIDS

[75] Inventor: David Thomas Parker, Livingston, N.J.

[73] Assignee: Novartis Corp., Summit, N.J.

[21] Appl. No.: 763,273

[22] Filed: Dec. 10, 1996

Related U.S. Application Data

[60] Provisional application No. 60/008,661 Dec. 15, 1995.

[51] Int. Cl.⁶ .................. A61K 31/19; A61K 31/44; C07C 311/15; C07D 211/70
[52] U.S. Cl. .................. 514/575; 514/357; 514/311; 514/428; 514/365; 514/372; 514/374; 514/378; 514/383; 514/381; 514/399; 514/438; 562/621; 546/337; 546/175; 548/567; 548/146; 548/215; 548/255; 549/72
[58] Field of Search .................. 562/621; 514/575, 514/357, 311, 428, 365, 372, 374, 378, 383, 381, 399, 438; 548/337, 567, 568, 146, 206, 215, 240, 255, 267.6, 253, 406, 338.1; 546/175; 549/72

[56] References Cited

U.S. PATENT DOCUMENTS

| | | | |
|---|---|---|---|
| 5,455,258 | 10/1995 | MacPherson et al. | 514/357 |
| 5,506,242 | 4/1996 | MacPherson et al. | 514/336 |
| 5,552,419 | 9/1996 | MacPherson et al. | 514/357 |
| 5,646,167 | 7/1997 | Macpherson et al. | 514/357 |

FOREIGN PATENT DOCUMENTS

| | | |
|---|---|---|
| 0606046 | 7/1994 | European Pat. Off. . |
| 9535276 | 12/1995 | WIPO . |
| 9600214 | 1/1996 | WIPO . |
| 9627583 | 9/1996 | WIPO . |

Primary Examiner—Deborah Lambkin
Attorney, Agent, or Firm—Norbert Gruenfeld

[57] ABSTRACT

Particularly the invention relates to the compounds of formula I

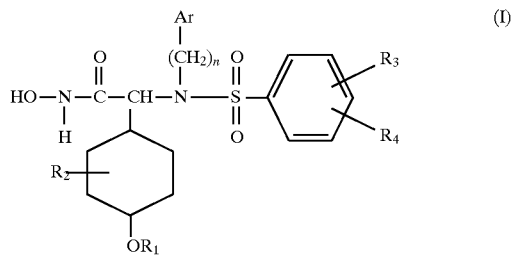

wherein
  Ar represents carbocyclic aryl, heterocyclic aryl or biaryl;
  $R_1$ represents lower alkyl, cycloalkyl, aryl-lower alkyl, lower alkoxy-lower alkyl, aryl, cycloalkyl-lower alkyl, halo-lower alkyl;
  $R_2$ represents hydrogen or lower alkyl;
  $R_3$ and $R_4$ represent independently hydrogen, lower alkyl, lower alkoxy, halo, hydroxy, acyloxy, lower alkoxy-lower alkoxy, trifluoromethyl or cyano; or $R_3$ and $R_4$ together represent lower allylenedioxy;
  n represents an integer from 1 to 5;
  pharmaceutically acceptable prodrug derivatives; and pharmaceutically acceptable salts thereof; methods for preparation thereof;
  pharmaceutical compositions comprising said compounds; and a method of inhibiting TNF-alpha activity and matrix-degrading metalloproteinases in mammals using such compounds.

23 Claims, No Drawings

CERTAIN ALPHA-SUBSTITUTED ARYLSULFONAMIDO ACETOHYDROXAMIC ACIDS

CROSS-REFERENCE TO RELATED APPLICATIONS

This application claims the benefit of provisional application Ser. No. 60/008,661 filed Dec. 15, 1995.

SUMMARY OF THE INVENTION

The present invention relates to novel alpha-(etherified cyclohexyl)-substituted arylsulfonamido acetohydroxamic acids and derivatives described below, as inhibitors of matrix-degrading metalloproteinases and TNF alpha (tumor necrosis factor alpha) activity, methods for preparation thereof, pharmaceutical compositions comprising said compounds, a method of inhibiting TNF alpha and matrix degrading metalloproteinase activity and a method of treating TNF alpha and matrix metalloproteinase dependent diseases or conditions in mammals which are responsive to matrix metalloprotease and TNF alpha inhibition, using such compounds or pharmaceutical compositions comprising such compounds of the invention.

The compounds of the invention are inhibitors of TNF-alpha converting enzyme (TNF-alpha convertase) and thus inhibit TNF alpha activity, e.g. suppress the production and/or release of TNF alpha, an important mediator of inflammation and tissue growth. Such properties render the compounds of the invention primarily useful for the treatment of tumors (malignant and non-malignant neoplasma) as well as of inflammatory conditions in mammals, e.g. for the treatment of arthritis (such as rheumatoid arthritis), septic shock, inflammatory bowel disease, Crohn's disease and the like.

The compounds of the invention also inhibit matrix degrading metalloproteinases such as gelatinase, stromelysin, collagenase, and macrophage metalloelastase. Thus the compounds of the invention inhibit matrix degradation and are also useful for the prevention or treatment of gelatinase-, stromelysin-, collagenase and macrophage metalloelastase-dependent pathological conditions in mammals. Such conditions include tumors (by inhibiting tumor growth, tumor metastasis, tumor progression or invasion and/or tumor angiogenesis), such tumors being e.g. breast, lung, bladder, colon, ovarian and skin cancer. Other conditions to be treated with the compounds of the invention include osteoarthritis, bronchial disorders (such as asthma by inhibiting the degradation of elastin), atherosclerotic conditions (by e.g. inhibiting rupture of atherosclerotic plaques), as well as acute coronary syndrome, heart attacks (cardiac ischemia), strokes (cerebral ischemias), restenosis after angioplasty, and also vascular ulcerations, ectasia and aneurysms.

Further conditions to be treated with the compounds of the invention are inflammatory demyelinating disorders of the nervous system in which myelin destruction or loss is involved (such as multiple sclerosis), optic neuritis, neuromyelitis optica (Devic's disease), diffuse and transitional sclerosis (Schilder's disease) and acute disseminated encephalomyelitis, also demyelinating peripheral neuropathies such as LandryGuilain-Barre-Strohl syndrome for motor defects; loss tissue ulceration (e.g. epidermal and gastric ulceration), abnormal wound healing, periodental disease, bone disease (e.g. Paget's disease and osteoporosis).

Ocular applications of the compounds of the invention include the treatment of ocular inflammation, corneal ulcerations, pterygium, keratitis, keratoconus, open angle glaucoma, retinopathies, and also their use in conjunction with refractive surgery (laser or incisional) to minimize adverse effects.

DETAILED DESCRIPTION OF THE INVENTION

The present invention relates to the 4etherified cyclohexyl- and arylsulfonamido-substituted hydroxamic acids of formula I

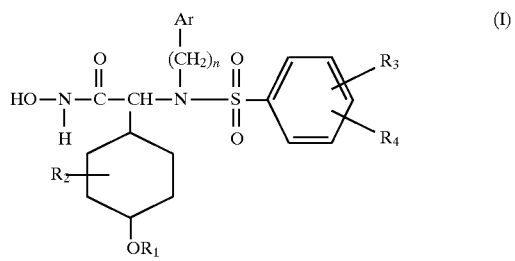

wherein
Ar represents carbocyclic aryl, heterocyclic aryl or biaryl;
$R_1$ represents lower alkyl, cycloalkyl, (carbocyclic or heterocyclic aryl)-lower alkyl, lower alkoxy-lower alkyl, carbocyclic aryl, heterocyclic aryl, cycloalkyl-lower alkyl or halo-lower alkyl;
$R_2$ represents hydrogen or lower alkyl;
$R_3$ and $R_4$ represent independently hydrogen, lower alkyl, lower alkoxy, halo, hydroxy, acyloxy, lower alkoxy-lower alkoxy, trifluoromethyl or cyano; or $R_3$ and $R_4$ together on adjacent carbon atoms represent lower alkylenedioxy;
n represents an integer from 1 to 5;
pharmaceutically acceptable prodrug derivatives thereof; and pharmaceutically acceptable salts thereof;
further to a process for the preparation of these compounds, to pharmaceutical compositions comprising these compounds, to the use of these compounds for the therapeutic treatment of the human or animal body or for the manufacture of a pharmaceutical composition.

The compounds of the invention depending on the nature of the substituents, possess one or more asymmetric carbon atoms. Also the cyclohexane substituents are either cis or trans to each other. The resulting diastereoisomers, enantiomers and geometric isomers are encompassed by the instant invention.

Preferred are the compounds of the invention wherein the configuration of the asymmetric carbon atom of the α-aminohydroxamic acid moiety to which is attached the cyclohexane ring corresponds to that of a D-amino acid precursor and is assigned the (R)-configuration.

Further preferred are the compounds of formula I which are trans 1,4-cyclohexane derivatives, i.e. in which the two 1,4-substituents are trans to each other.

Pharmaceutically acceptable prodrug derivatives are those that may be convertible by solvolysis or under physiological conditions to the free hydroxamic acids of the invention and represent such hydroxamic acids in which the CONHOH group is derivatized in form of an O-acyl or an optionally substituted O-benzyl derivative. Preferred are the optionally substituted O-benzyl derivatives.

Prodrug acyl derivatives are preferably those derived from an organic carbonic acid, an organic carboxylic acid or a carbamic acid.

An acyl derivative which is derived from an organic carboxylic acid is, for example, lower alkanoyl, phenyl-lower alkanoyl or unsubstituted or substituted aroyl, such as benzoyl.

An acyl derivative which is derived from an organic carbonic acid is, for example, alkoxycarbonyl, especially lower alkoxycarbonyl, which is unsubstituted or substituted by carbocyclic or heterocyclic aryl or is cycloalkoxycarbonyl, especially $C_3$–$C_7$-cycloalkyloxycarbonyl, which is unsubstituted or substituted by lower alkyl.

An acyl derivative which is derived from a carbamic acid is, for example, amino-carbonyl which is substituted by lower alkyl, carbocyclic or heterocyclic aryl-lower alkyl, carbocyclic or heterocyclic aryl, lower allylene or lower alkylene interrupted by O or S.

Prodrug optionally substituted O-benzyl derivatives are preferably benzyl or benzyl mono-, di-, or tri-substituted by e.g. lower alkyl, lower alkoxy, amino, nitro, halogen and/or trifluoromethyl.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The general definitions used herein have the following meaning within the scope of the present invention, unless otherwise specified.

The term "lower" referred to above and hereinafter in connection with organic radicals or compounds respectively defines such as branched or unbranched with up to and including 7, preferably up to and including 4, and advantageously one or two carbon atoms.

A lower alkyl group is branched or unbranched and contains 1 to 7 carbon atoms, preferably 1-4 carbon atoms, and represents for example methyl, ethyl, propyl, butyl, isopropyl or isobutyl. Lower alkyl for R, is preferably $C_2$–$C_5$-alkyl, advantageously $C_2$–$C_4$-alkyl.

A lower alkoxy (or alkyloxy) group preferably contains 1–4 carbon atoms, and represents for example methoxy, ethoxy, propoxy, isopropoxy, butoxy or isobutoxy.

Halogen (or halo) preferably represents chloro or fluoro but may also be bromo or iodo. Aryl represents carbocyclic or heterocyclic aryl.

Carbocyclic aryl represents monocyclic or bicyclic aryl, for example phenyl or phenyl mono-, di- or tri-substituted by one, two or three radicals selected from lower alkyl, lower alkoxy, hydroxy, halogen, cyano, trifluoromethyl, lower alkylenedioxy and oxy-$C_2$–$C_3$-alkylene; or 1- or 2-naphthyl. Lower alkylenedioxy is a divalent substituent attached to two adjacent carbon atoms of phenyl, e.g. methylenedioxy or ethylenedioxy. Oxy-$C_2$–$C_3$-alkylene is also a divalent substituent attached to two adjacent carbon atoms of phenyl, e.g. oxyethylene or oxypropylene. An example for oxy-$C_2$–$C_3$-alkylene-phenyl is 2,3-dihydrobenzofuran-5-yl.

Preferred as carbocyclic aryl is phenyl or phenyl mono-substituted by lower alkoxy, halogen, lower alkyl or trifluoromethyl, especially phenyl or phenyl monosubstituted by lower alkoxy, halogen or trifluoromethyl, and in particular phenyl.

Heterocyclic aryl represents monocyclic or bicyclic heteroaryl, for example pyridyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl, or any said radical substituted, especially mono- or di-substituted, by e.g. lower alkyl or halogen. Pyridyl represents 2-, 3- or 4-pyridyl, advantageously 3- or 4-pyridyl. Thienyl represents 2- or 3-thienyl, advantageously 2-thienyl. Quinolinyl represents preferably 2-, 3- or 4-quinolinyl, advantageously 2-quinolinyl. Isoquinolinyl represents preferably 1-, 3- or 4-isoquinolinyl. Benzopyranyl, benzothiopyranyl represent preferably 3-benzopyranyl or 3-benzothiopyranyl, respectively. Thiazolyl represents preferably 2- or 4-thiazolyl, advantageously 4-thiazolyl. Triazolyl is preferably 1-, 2- or 5-(1,2,4-triazolyl). Tetrazolyl is preferably 5-tetrazolyl. Inidazolyl is preferably 4-imidazolyl.

Preferably, heterocyclic aryl is pyridyl, quinolinyl, pyrrolyl, thiazolyl, isoxazolyl, triazolyl, tetrazolyl, pyrazolyl, imidazolyl, thienyl, or any said radical substituted, especially mono- or di-substituted, by lower alkyl or halogen; and in particular pyridyl.

Biaryl is preferably carbocyclic biaryl, e.g. biphenyl, namely 2-, 3- or 4-biphenyl, advantageously 4-biphenyl, each optionally substituted by e.g. lower alkyl, lower alkoxy, halogen, trifluoromethyl or cyano.

Cycloalkyl represents a saturated cyclic hydrocarbon optionally substituted by lower alkyl which contains 3 to 10 ring carbons and is advantageously cyclopentyl, cyclohexyl, cycloheptyl or cyclooctyl optionally substituted by lower alkyl.

Carbocyclic aryl-lower alkyl represents preferably straight chain or branched aryl-$C_1$–$C_4$-alkyl in which carbocyclic aryl has meaning as defined above, e.g. benzyl or phenyl-(ethyl, propyl or butyl), each unsubstituted or substituted on phenyl ring as defined under carbocyclic aryl above, advantageously optionally substituted benzyl.

Heterocyclic aryl-lower alkyl represents preferably straight chain or branched heterocyclic aryl-$C_1$–$C_4$-alkyl in which heterocyclic aryl has meaning as defined above, e.g. 2-, 3- or 4-pyridylmethyl or (2-, 3- or 4-pyridyl)-(ethyl, propyl or butyl); or 2- or 3-thienylmethyl or (2- or 3-thienyl)-(ethyl, propyl or butyl); 2-, 3- or 4-quinolinylmethyl or (2-, 3- or 4-quinolinyl)-(ethyl, propyl or butyl); or 2- or 4-thiazolylmethyl or (2- or 4thiazolyl)-(ethyl, propyl or butyl).

Cycloalkyl-lower alkyl represents e.g. (cyclopentyl- or cyclohexyl)-(methyl or ethyl).

Acyl is derived from an organic carboxylic acid, carbonic acid or carbamic acid.

Acyl represents e.g. lower alkanoyl, carbocyclic aryl-lower alkanoyl, lower alkoxycarbonyl, aroyl, di-lower alkylaminocarbonyl or di-lower alkylamino-lower alkanoyl. Preferably, acyl is lower alkanoyl.

Lower alkanoyl represents e.g. $C_1$–$C_7$-alkanoyl including formyl, and is preferably $C_2$–$C_4$-alkanoyl such as acetyl or propionyl.

Aroyl represents e.g. benzoyl or benzoyl mono- or di-substituted by one or two radicals selected from lower alkyl, lower alkoxy, halogen, cyano and trifluoromethyl; or 1- or 2,naphthoyl; and also e.g. pyridylcarbonyl.

Lower alkoxycarbonyl represents preferably $C_1$–$C_4$-alkoxycarbonyl, e.g. ethoxycarbonyl.

Lower alkylene represents either straight chain or branched alkylene of 1 to 7 carbon atoms and represents preferably straight chain alkylene of 1 to 4 carbon atoms, e.g. a methylene, ethylene, propylene or butylene chain, or said methylene, ethylene, propylene or butylene chain mono-substituted by $C_1$–$C_3$-alkyl (advantageously methyl) or disubstituted on the same or different carbon atoms by $C_1$–$C_3$-alkyl (advantageously methyl), the total number of carbon atoms being up to and including 7.

Lower alkylenedioxy is preferably ethylenedioxy or methylenedioxy.

Esterified carboxyl is for example lower alkoxycarbonyl or benzyloxycarbonyl.

Amidated carboxyl is for example aminocarbonyl, mono- or di-lower alkylaminocarbonyl.

A particular embodiment of the invention consists of the compounds of formula I in which the asymmetric carbon of the α-aminohydroxamic acid moiety is of the (R)-configuration, namely compounds of formula II

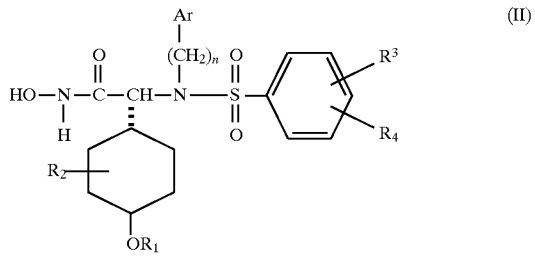

wherein Ar, $R_1$, $R_2$, $R_3$ and $R_4$ have meaning as defined above, pharmaceutically acceptable prodrug derivatives thereof and pharmaceutically acceptable salts thereof.

A further embodiment represents the above compounds having the trans configuration with respect to the 1,4-substituents on the cyclohexane ring, particularly those of formula III

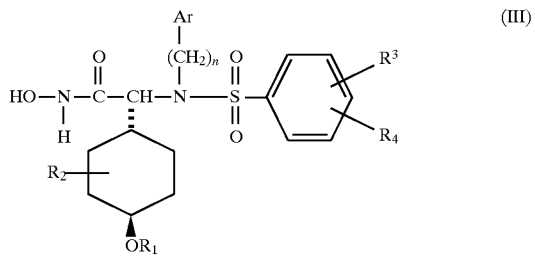

wherein

Ar represents carbocyclic or heterocyclic aryl;

$R_1$ represents lower alkyl, cycloalkyl, (carbocyclic or heterocyclic aryl)-lower alkyl or lower alkoxy-lower alkyl;

$R_2$ represents hydrogen or lower alkyl;

$R_3$ is hydrogen, lower alkoxy or halogen;

$R_4$ is hydrogen or lower alkoxy; or $R_3$ and $R_4$ together on adjacent carbon atoms represent methylenedioxy; and n is 14;

pharmaceutically acceptable prodrug derivatives thereof; and pharmaceutically acceptable salts thereof.

Also preferred are said compounds of formula III wherein Ar represents heterocyclic aryl; $R_1$ represents lower alkyl, cycloalkyl or lower alkoxy-lower alkyl; $R_2$ represents hydrogen or lower alkyl; $R_3$ and $R_4$ are hydrogen or lower alkoxy; and n is 1–4; pharmaceutically acceptable prodrug derivatives thereof; and pharmaceutically acceptable salts thereof.

Preferred are said compounds wherein $R_3$ is at the para position and $R_4$ is at the meta position.

Further preferred are the said compounds of formula m wherein Ar is heterocyclic aryl; $R_1$ is lower alkyl; $R_2$ is hydrogen; $R_3$ is para-lower alkoxy; $R_4$ is hydrogen; and n is 1 or 2; and pharmaceutically acceptable salts thereof.

Particularly preferred are compounds of formula III wherein Ar is pyridyl, especially 3- or 4-pyridyl; $R_1$ is lower alkyl, especially straight chain $C_2$–$C_5$-alkyl; $R_2$ and $R_4$ are hydrogen, $R_3$ is para-lower alkoxy; and n is 1; and pharmaceutically acceptable salts thereof.

Further preferred are said compounds wherein Ar is 4-pyridyl; $R_1$ is $C_2$–$C_4$alkyl; $R_2$ and $R_4$ are hydrogen; $R_3$ is para-ethoxy; and n is 1; and pharmaceutically acceptable salts thereof.

A particular embodiment of the invention relates to compounds of formula I, I or HI respectively wherein $R_1$ is $C_2$–$C_7$alkyl, in particular $C_2$–$C_5$alkyl, preferably $C_2$–$C_4$alkyl.

The invention relates especially to the specific compounds described in the examples, pharmaceutically acceptable prodrug derivatives thereof and pharmaceutically acceptable salts thereof, and in particular to the specific compounds described in the examples and pharmaceutically acceptable salts thereof.

The compounds of the invention exhibit valuable pharmacological properties in mammals including man.

Firstly, they are inhibitors of TNF-alpha converting enzyme CINF-alpha convertase) and thus inhibit TNF-alpha activity, e.g. suppress the production and/or release of TNF alpha, an important mediator of inflammation and tissue growth. Such properties render the compounds of the invention primarily useful for the treatment of tumors (malignant and non-malignant neoplasms) as well as of inflammatory conditions in mammals, e.g. for the treatment of arthritis (such as rheumatoid arthritis), septic shock, inflammatory bowel disease, Crohn's disease and the like.

Further, the compounds of the invention also inhibit matrix degrading metalloproteinase enzymes such as gelatinase, stromelysin, collagenase, and macrophage metalloelastase. Thus the compounds of the invention inhibit matrix degradation and are also useful for the treatment of gelatinase-, stromelysin-, collagenase- and macrophage metahoelastase-dependent pathological conditions in mammals. Such conditions include tumors (by inhibiting tumor growth, tumor metastasis, tumor progression or invasion and/or tumor angiogenesis), such tumors being e.g. breast, lung, bladder, colon, ovarian and skin cancer. Other conditions to be treated with the compounds of the invention include osteoarthritis, bronchial disorders (such as asthma by inhibiting the degradation of elastin), atherosclerotic conditions (by e.g. inhibiting rupture of atherosclerotic plaques), as well as acute coronary syndrome, heart attacks (cardiac ischemia), strokes (cerebral ischemias), and restenosis after angioplasty.

Further conditions to be treated with the compounds of the invention are inflammatory demyelinating disorders of the nervous system in which myelin destruction or loss is involved (such as multiple sclerosis), optic neuritis, neuromyelitis optica (Devic's disease), diffuse and transitional sclerosis (Schilder's disease) and acute disseminated encephalomyelitis, also demyelinating peripheral neuropathies such as LandryGuillain-Barre-Strohl syndrome for motor defects; also tissue ulceration (e.g. epidermal and gastric ulceration), abnormal wound healing, periodontal disease, bone disease (e.g. Paget's disease and osteoporosis).

Ocular applications of the compounds of the invention include the treatment of ocular inflammation, corneal ulcerations, pterygium, keratitis, keratoconus, open angle glaucoma, retinopathies, and also their use in conjunction with refractive surgery (laser or incisional) to minimize adverse effects.

The compounds are particularly useful for the treatment of inflammatory conditions, such as rheumatoid arthritis, and of tumors.

Beneficial effects are evaluated in pharmacological tests generally known in the art, and as illustrated herein.

The above-cited properties are demonstrable in in vitro and in vivo tests, using advantageously mammals, e.g. rats, guinea pigs, dogs, rabbits, or isolated organs and tissues, as well as mammalian enzyme preparations. Said compounds can be applied in vitro in the form of solutions, e.g. preferably aqueous solutions, and in vivo either enterary or parenterally, advantageously orally, e.g. as a suspension or in aqueous solution. The dosage in vitro may range between about $10^{-5}$ molar and $10^{-10}$ molar concentrations. The dosage in vivo may range, depending on the route of administration, between about 0.1 and 100 mg/kg.

The inhibition of the production and secretion of TNF-alpha (by inhibition of TNF-α convertase) can be determined e.g. as described in Nature 370, 555, 558 (1994).

The effect on the production of soluble TNF-alpha by LPS-stimulated THP-1 cells can be determined as follows:

Tissue culture medium used is RPM 1640 (Gibco cat #11875-036) containing 10% fetal calf serum, 1% penicillin and streptomycin. TBP-1 cells (ATCC #202-TIB) at 1×10+5 cells/well are added to 100 μl medium or test compound. Cells are pre-incubated with compound for 30 minutes in a 37° C. humidified chamber with 5% $CO_2$ and then stimulated with 100 ng/ml of LPS (Sigma cat #L-4391) for 4 hours. Plates are then centrigued and 100 SLW of conditioned medium for TNF analysis is harvested. The amount of TNF-alpha in control and test cultures is determined by ELISA using recombinant TNF-alpha for the standard curve, using TNF ELISA plates (Genzyme) for TNF analysis. Absorbance readings and data calculations are performed on a Molecular Devices plate reader. Results are expressed in $IC_{50}$'s of test compound.

Illustrative of the invention, the compounds of example 1 and example 2(u) exhibit an $IC_{50}$ of about 2.5 μm in the above assay.

The effect on the plasma concentration of TNF-alpha in the mouse following intravenous injection of endotoxin can be determined as follows:

Female Balb-CbyJ mice are dosed by gavage with test compound in 0.1 ml cornstarch vehicle/10 grams body weight. One to four hours after administration of test compound, 0.1 mg/kg Lipopolysaccharide from *E. coli* 0127:B8 (Difco #3880-25-0) in saline is injected i.v. One hour after i.v. injection of LPS, blood is collected for determination of plasma TNF-alpha using mouse TNF-alpha ELISA kit (Genzyme). Eight mice are used per treatment group. Results are expressed as % inhibition of mean TNF-alpha concentration in control mice.

Illustrative of the invention, the compound of example 1 gives 50% inhibition in the above assay at a dose of about 50 mg/Kg p.o.

The effect on the synovial fluid concentration of TNF-alpha in an inflamed rat knee can be determined as follows:

Female lewis rats are dosed by gavage with test compound in 0.1 ml cornstarch vehicle. One to four hours after administration of test compound 0.1 mg Lipopolysaccharide from *E. coli* 0127:B8 (Difco #3880-25-0) is injected into both knees. Two hours after intra-articular LPS injection, knees are lavaged with 0.1 ml saline and 2 lavages from same rat are pooled. TNF-alpha is measured using mouse TNF-alpha ELISA kit (Genzyme) which crossreacts with rat TNF-alpha Results are expressed as % inhibition of mean TNF-alpha concentration in synovial fluid from saline-injected knees.

Illustrative of the invention the compounds of examples 1 and 2(u) reduce TNF-α concentration in the synovial fluid from saline-injected knees by about 70% and 98%, respectively, at a dose of 50 mg/Kg p.o.

Antiinflammatory activity can be determined in standard inflammation and arthritic animal models well-known in the art, e.g. the adjuvant arthritis model in rats and the collagen II induced arthritis model in mice [Mediators of Inflam. 1, 273-279 (1992)].

Illustrative of the invention, the compounds of examples 1 and 2(u) are effective in inhibiting collagen-II induced arthritis in mice at a dose of 100 mg/Kg p.o.

One test to determine the inhibition of stromelysin activity is based on its hydrolysis of Substance P using a modified procedure of Harrison et al (Harrison, R. A., Teahan J., and Stein R., A semicontinuous, high performance chromatography based assay for stromelysin, Anal. Biochem. 18, 110–113 (1989)). In this assay, Substance P is hydrolyzed by recombinant human stromelysin to generate a fragment, Substance P 7-11, which can be quantitated by HPLC. In a typical assay, a 10 mM stock solution of a compound to be tested is diluted in the assay buffer to 50 μM, mixed 1:1 with 8 μg recombinant human stromelysin (mol. wt. 45–47 kDa, 2 Units; where 1 Unit produces 20 mmoles of Substance P 7-11 in 30 minutes) and incubated along with 0.5 mM Substance P in a final volume of 0.125 ml for 30 minutes at 37° C. The reaction is stopped by adding 10 mM EDTA and Substance P 7-11 is quantified on RP-8 HPLC. The $IC_{50}$ for inhibition of stromelysin activity and Ki are calculated from control reaction without the inhibitor.

Illustrative of the invention, the compound of example 1 exhibits an $IC_{50}$ of about 16 nM in the assay. For the compound of example 2(u), the $IC_{50}$ is about 11 nM.

Stromelysin activity can also be determined using human aggrecan as a substrate. This assay allows the confirmation in-vitro that a compound can inhibit the action of stromelysin on its highly negatively-charged natural substrate, aggrecan (large aggregating prtoeoglycan). Within the cartilage, proteoglycan exists as an aggregate bound to hyaluronate. Human proteoglycan aggregated to hyaluronate is used as an enzyme substrate. The assay is set up in 96-well microtiter plates allowing rapid evaluation of compounds. The assay has three major steps:

1) Plates are coated with hyaluronate (human umbilical chord, 400 ug/ml), blocked with BSA (5 mg/ml), and then proteoglycan (human articular cartilage D1—chondroitinase ABC digested, 2 mg/ml) is bound to the hyaluronate. Plates are washed between each step.

2) Buffers+inhibitor (1 to 5,000 nM)+recombinant human stromelysin (1–3 Units/well) are added to wells. The plates are sealed with tape and incubated overnight at 37° C. The plates are then washed.

3) A primary (3B3) antibody (mouse IgM, 1:10,000) is used to detect remaining fragments. A secondary antibody, peroxididase-linked anti-IgM, is bound to the primary antibody. OPD is then added as a substrate for the peroxidase and the reaction is stopped with sulfuric acid. The $IC_{50}$ for inhibition of stromelysin activity is graphically derived and Ki is calculated.

Collagenase activity is determined as follows: ninety six-well, flat-bottom microtiter plates are first coated with bovine type I collagen (35 ug/well) over a two-day period at 30° C. using a humidified and then dry atmosphere; plates are rinsed, air dried for 34 hours, sealed with Saran wrap and stored in a refrigerator. Human recombinant fibroblast collagenase and a test compound (or buffer) are added to wells (total volume =0.1 ml) and plates are incubated for 2 hours at 35° C. under humidified conditions; the amount of collagenase used per well is that causing approximately 80% of maximal digestion of collagen. The incubation media are removed from the wells, which are then rinsed with buffer, followed by water. Coomasie blue stain is added to the wells for 25 minutes, removed, and wells are again rinsed with water. Sodium dodecyl sulfate (20% in 50% dimethylformamide in water) is added to solubilize the remaining stained collagen and the optical density at 570 nM wave length is measured. The decrease in optical density due to collagenase (from that of collagen without enzyme) is compared to the decrease in optical density due to the enzyme in the presence of test compound, and percent inhibition of enzyme activity is calculated. IC50's are determined from a range of concentrations of inhibitors (4–5 concentrations, each tested in triplicate), and $K_i$ values are calculated.

Illustrative of the invention, the compounds of examples 1 and 2(u) exhibit an $IC_{50}$ of about 80 and 45 nM, respectively.

The effect of compounds of the invention in-vivo can be determined in rabbits. Typically, four rabbits are dosed orally with a compound up to four hours before being injected intra-articularly in both knees (N=8) with 40 Units of recombinant human stromelysin dissolved in 20 mM Tris, 10 mM $CaCl_2$, and 0.15 M NaCa at pH 7.5. Two hours later the rabbits are sacrificed, synovial lavage is collected, and keratan sulfate (KS) and sulfated glycosarninoglycan (S-GAG) fragments released into the joint are quantitated. Keratan sulfate is measured by an inhibition ELISA using the method of Thonar (Thonar, E. J.-M. A., Lenz, M. E., Klinsworth, G. K., Caterson, B., Pachman, L. M., Glicknian, P., Katz, R., Huff, J., Keuttner, K. E. Quantitation of keratan sulfate in blood as a marker of cartilage catabolism, Arthr. Rheum. 28, 1367–1376 (1985)). Sulfated glycosaminoglycans are measured by first digesting the synovial lavage with streptomyces hyaluronidase and then measuring DMB dye binding using the method of Goldberg (Goldberg, R.L. and Kolibas, L. An improved method for determining proteoglycan synthesized by chondrocytes in culture. Connect. Tiss. Res. 24,, 265–275 (1990)). For an i.v. study, a compound is solubilized in 1 ml of PEG-400, and for a p.o. study, a compound is administered in 5 ml of fortified corn starch per kilogram of body weight.

The effect in protecting against cartilage degradation in arthritic disorders can be determined e.g. in a surgical model of osteoarthritis described in Arthritis and Rheumatism, Vol. 26, 875–886 (1983).

The effect on ulcerations, e.g. ocular ulcerations, can be determined in the rabbit by measuring the reduction of corneal ulceration following an alkali burn to the cornea.

Macrophage metalloelastase (MME) inhibitory activity can be determined by measuring the inhibition of the degradation of [$^3$H]-elastin by truncated recombinant mouse macrophage metalloelastase as follows:

About 2 ng of recombinant truncated mouse macrophage metalloelastase (FASEB Journal Vol. 8, A151, 1994), purified by QSepharose column chromatography is incubated with test compounds at the desired concentrations in the presence of 5 mM $CaCl_2$, 400 nM NaCl, [$^3$H]elastin (60,000 cpm/tube), and 20 mM Tris, pH 8.0, at 37° C. overnight. The samples are spun in a microfuge centrifuge at 12,000 rpm for 15 minutes. An aliquot of the supernatant is counted in a scintillation counter to quantitate degraded [$^3$H]elastin. $IC_{50}$'s are determined from a range of concentrations of the test compounds and the percent inhibition of enzyme activity obtained.

The effect of the compounds of the invention for the treatment of emphysema can be determined in animal models described in American Review of Respiratory Disease 117, 1109 (1978).

The antitumor effect of the compounds of the invention can be determined e.g. by measuring the growth of human tumors implanted subcutaneously in Balb/c nude treated mice according to methodology well-known in the art in comparison to placebo treated mice. Illustrative tumors are e.g. estrogen dependent human breast carcinoma BT20 and MCF7, human bladder carcinoma 124, human colon carcinoma Colo 205, human lung adenocarcinoma A549 and human ovarian carcinoma NIH-OVCAR3.

The effect on tumor angiogenesis can be determined e.g. in rats implanted with Walker 256 carcinoma in pellets to stimulate angiogenesis from vessels of the limbus, as described by Galardy et al, Cancer Res. 54,4715 (1994). The effect of the compounds of the invention on atherosclerotic conditions can be evaluated using atherosclerotic plaques from cholesterol-fed rabbits which contain activated matrix metalloproteinases as described by Sukhova et al, Circulation 90 I404 (1994). The inhibitory effect on matrix metalloproteinase enzyme activity in rabbit atherosclerotic plaques can be determined by in situ zymography, as described by Galis et al, J. Clin. Invest. 94, 2493 (1994), and is indicative of plaque stabilization (inhibition of plaque rupture).

The effect on vascular aneurysms, e.g. the inhibition of aneurysm formation, can be determined in experimental models such as Apo-E transgenic mice and/or LDL receptor knockout mice.

The effect on restenosis and vascular remodeling can be evaluated in the rat ballooned carotid artery model.

The effect on demyelinating disorders of the nervous system, such as multiple sclerosis, can be evaluated by measuring the reversal of experimental antiimmune encephalo-myelitis in mice, e.g. as described by Gijbels et al, J. Clin. Invest. 94, 2177 (1994).

As inhibitors of TNF-alpha convertase and matrix metalloproteinases the compounds of the invention are particularly useful in mammals as antiinflammatory agents for the treatment of e.g. osteoarthritis, rheumatoid arthritis, as antitumor agents for the treatment and prevention of tumor growth, tumor metastasis, tumor invasion or progression, and as antiatherosclerotic agents for the treatment and prevention of the rupture of atherosclerotic plaques.

The compounds of formula I can be prepared e.g. by condensing a carboxylic acid of formula IV

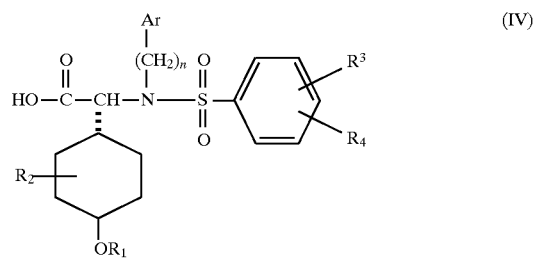

or a reactive functional derivative thereof, wherein Ar, n and $R_1-R_4$ having meaning as defined hereinabove, with hydroxylamine of formula V,

optionally in protected form, or a salt thereof;

and, if necessary, temporarily protecting any interfering reactive group(s), and then liberating the resulting compound of the invention; and, if required or desired, converting a resulting compound of the invention into another compound of the invention, and/or, if desired, converting a resulting free compound into a salt or a resulting salt into a free compound or into another salt; and/or separating a mixture of isomers or racemates obtained into the single isomers or racemates; and/or, if desired, resolving a racemate into the optical antipodes.

In starting compounds and intermediates which are converted to the compounds of the invention in a manner described herein, functional groups present, such as amino, carboxyl and hydroxy groups, are optionally protected by conventional protecting groups that are common in preparative organic chemistry. Protected amino, carboxyl and hydroxy groups are those that can be converted under mild conditions into free amino and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis", Wiley, New York, 1991.

In the processes cited herein, reactive functional derivatives of carboxylic acids represent, for example, anhydrides especially mixed anhydrides, acid halides, acid azides, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters for example succinimido, phthalimido or 4-nitrophenyl esters; lower alkyl esters are for example the methyl or ethyl esters.

Also, a reactive esterified derivative of an alcohol in any of the reactions cited herein represents said alcohol esterified by a strong acid, especially a strong inorganic acid, such as a hydrohalic acid, especially hydrochloric, hydrobromic or hydroiodic acid, or sulphuric acid, or by a strong organic acid, especially a strong organic sulfonic acid, such as an aliphatic or aromatic sulfonic acid, for example methanesulfonic acid, 4-methylbenzenesulfonic acid or 4-bromobenzenesulfonic acid. A said reactive esterified derivative is especially halogen, for example chloro, bromo or iodo, or aliphatically or aromatically substituted sulfonyloxy, for example methanesulfonyloxy, 4-methylbenzenesulfonyloxy (tosyloxy) or trifluoromethanesulfonyloxy.

The above process for the synthesis of compounds of the invention can be carried out according to methodology generally known in the art for the preparation of hydroxamic acids and derivatives thereof.

The synthesis according to the above process (involving the condensation of a free carboxylic acid of formula IV with an optionally hydroxy protected hydroxylamine derivative of formula V can be carried out in the presence of a condensing agent, e.g. 1,1'-carbonyldiimidazole, or N-(dimethylaminopropyl)-N'-ethylcarbodiimide or dicyclohexylcarbod mide, with or without 1-hydroxybenzotriazole in an inert polar solvent, such as dimethylformamide or dichloromethane, preferably at room temperature.

The synthesis involving the condensation of a reactive functional derivative of an acid of formula IV as defined above, e.g. an acid chloride or mixed anhydride with optionally hydroxy protected hydroxylamine, or a salt thereof, in presence of a base such as triethylamine can be carried out, at a temperature ranging preferably from about −78° C. to +75° C., in an inert organic solvent such as dichloromethane or toluene.

Protected forms of hydroxylamine (of formula V) in the above process are those wherein the hydroxy group is protected for example as a t-butyl ether, a benzyl ether, a triphenylmethyl ether, a tetrahydropyranyl ether, or as a trimethylsilyl derivative. Removal of said protecting groups is carried out according to methods well known in the art, e.g. hydrogenolysis or acid hydrolysis. Hydroxylamine is preferably generated in situ from a hydroxylamine salt, such as hydroxylamine hydrochloride.

The starting carboxylic acids of formula IV can be prepared as follows:

An amino acid of formula VI

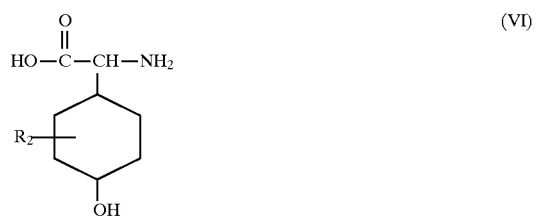

wherein $R_2$ is hydrogen or lower alkyl, which is optionally esterified e.g. with a lower alkanol (such as methanol) or with benzyl alcohol, is treated with a reactive functional derivative of the appropriate sulfonic acid of the formula VII

wherein $R_3$ and $R_4$ have meaning as defined hereinabove, e.g. with the corresponding sulfonyl chloride, in the presence of a suitable base, such as triethylamine or dicyclohexylamine, using a polar solvent such as tetrahydrofuran, dioxane or acetonitrile to obtain a compound of the formula VIII

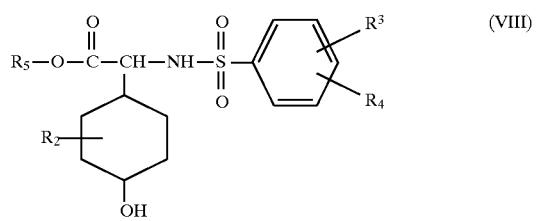

wherein $R_2$–$R_4$ have meaning as defined above and $R_5$ is hydrogen or a carboxyl protecting group, e.g. lower alkyl or benzyl.

The starting materials of formula VI, VII and XII are either known in the art, or can be prepared by methods well-known in the art or as described herein.

Optically active D-amino acids of formula VI (the R-enantiomers) can be prepared according to methods known in the art, e.g. according to methods described in Coil. Czech. Comm. 49, 712–742 (1984) and Angew. Chem. Int. Ed (Engl.) 27, 1194 (1988).

The intermediates of formula VIII can be converted to the intermediates of formula IX

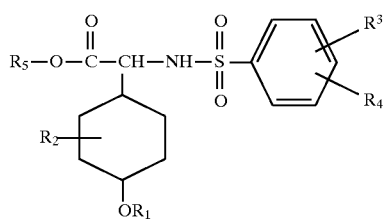

(IX)

wherein $R_1$–$R_5$ having meaning as defined above, by treatment with a reactive esterified derivative of the alcohol of the formula

 (X)

wherein $R_1$ has meaning as defined in formula I, under conditions well known in the art for ether formation.

Alternatively, the ether intermediates of formula IX can be prepared by reduction of ketone compounds of formula XI

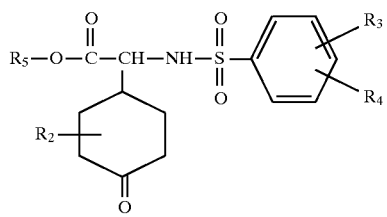

(XI)

wherein $R_2$–$R_5$ have meaning as defined in formula VIII, in the presence of an alcohol of formula X ($R_1$–OH). The reductive O-alkylation can be carried out essentially as described in J. Am. Chem. Soc. 94, 3659 (1972), using mono-, di- or trialkyisilanes or mono-, di- or triarylsilanes in acidic medium, e.g. in the presence of trfuoroacetic acid. The resulting cis and trans isomers can be separated by known methods, such as chromatography on silica gel.

Alternatively, the ketone intermediates of formula XI wherein $R_2$ is hydrogen can be converted to the tertar alcohol intermediates of formula VIII wherein $R_2$ is lower alkyl (and $R_2$ and $OR_1'$ are located on the same carbon atom) according to conventional methods, and such are subsequently etherified with a reactive esterified derivative of $R_1$—OH, such as the trifluoromiethanesulfonyl derivative.

The ketones of formula XI can in turn be prepared by oxidation of alcohols of formula VIHI by treatment with e.g. sodium hypochiorite in the presence of a free radical, e.g. TEMPO (2,2,6,6-tetramethyl-1-piperidinyloxy free radical).

Treatment of an intermediate of formula IX with a reactive esterified derivative (such as the halide, e.g. the chloride, bromide or iodide derivative) of the alcohol of the formula XII

 (XII)

wherein Ar and n have meaning as defined herein, in the presence of an appropriate base, such as potassium carbonate or dicyclohexylamine, in a polar solvent, such as dimethylformamide yields an ester of a compound of formula IV. The ester can then be converted to the acid of formula IV, using either hydrogenolysis or standard mild methods of ester hydrolysis, preferably under acidic conditions, the method depending on the nature of the esterifying group.

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials and processes for their manufacture.

Depending on the choice of starting materials and methods, the new compounds may be in the form of one of the possible isomers or mixtures thereof, for example, as substantially pure geometric (cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. The hydroxamic acids or carboxylic acid intermediates can thus be resolved into their optical antipodes e.g. by fractional crystallization of d- or l-(alphamethylbenzylamine, cinchonidine, cinchonine, quinine, quinidine, ephedrine, dehydroabietylamine, brucine or strychnine)-salts.

Finally, acidic compounds of the invention are either obtained in the free form, or as a salt thereof.

Acidic compounds of the invention may be converted into salts with pharmaceutically acceptable bases, e.g. an aqueous alkali metal hydroxide, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_{1-4}$)-alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as ($C_1$–C4)-alkane- or arylsulfonic acids which are unsubstituted or substituted, for example, by halogen, for example methanesulfonic acid.

Preferred are salts formed with hydrochloric acid, methanesulfonic acid and maleic acid.

In view of the close relationship between the free compounds and the compounds in the form of their salts, whenever a compound is refereed to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for eternal, such as oral or rectal, transdermal and parenteral administration to mammals, including man, to inhibit TNF-alpha converting enzyme and matrix-degrading metaloproteinases, and for the treatment of disorders responsive thereto, comprising an effective amount of a pharmacologically active compound of the invention, alone or in combination, with one or more pharmaceutically acceptable cartiers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable formulations for topical application, e.g. to the skin and eyes, are preferably aqueous solutions, ointments, creams or gels well-known in the art.

The pharmaceutical formulations contain an effective TNF-alpha convertase inhibiting amount and/or matrix-degrading metaloproteinase inhibiting amount of a compound of the invention as defined above, either alone or in combination with another therapeutic agent, e.g. an anti-inflammatory agent with cyclooxygenase inhibiting activity, or other antirheumatic agents such as methotrexate, each at an effective therapeutic dose as reported in the art. Such therapeutic agents are well-known in the art.

Examples of antiinflammatory agents with cyclooxygenase inhibiting activity are diclofenac, naproxen, ibuprofen, and the like.

In conjunction with another active ingredient, a compound of the invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 10 and 1000 mg, advantageously between about 25 and 250 mg of the active ingredient.

The present invention also relates to methods of using the compounds of the invention and their pharmaceutically acceptable salts, or pharmaceutical compositions thereof, in mammals for inhibiting TNF-alpha activity and inhibiting the matrix-degrading metalloproteinases, e.g. stromelysin, gelatinase, collagenase and macrophage metalloelastase, for inhibiting tissue matrix degradation, and for the treatment of TNF-alpha and matrix-degrading metalloproteinase dependent conditions as described herein, e.g. inflammation, rheumatoid arhritis, osteoatis, also tumors (tumor growth, metastasis, progression or invasion), pulmonary disorders, atherosclerosis and the like described herein. Tumors (carcinomas) include mammalian breast, lung, bladder, colon, prostate and ovarian cancer, and skin cancer, including melanoma and Kaposi's sarcoma.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20–133 mbar). The structure of final products, intermediates and starting materials is confirmed by standard analytical methods, e.g. microanalysis and spectroscopic characteristics (e.g. MS, IR, NMR). Abbreviations used are those conventional in the art. The concentration for $[\alpha]_D$ determinations is expressed in mg/ml.

EXAMPLE 1

N-(t-Butyloxy)-2(R)-[(4-methoxybenzenesulfonyl)(4-picolyl)amino]-2-(trans-4-propoxycyclohexyl) acetamide (0.84 g, 1.5 mmol) is dissolved in dichloroethane (50 mL) containing ethanol (0.1 mL, 1.5 mmol) in a round bottom flask, and the reaction is cooled to −10° C. Hydrochloric acid gas (from a lecture bottle) is bubbled through for 10 minutes. The reaction is sealed, allowed to slowly warm to room temperature and stirred for 4 days. The solvent is reduced to ⅓ volume by evaporation and triturated with ether. The mixture is filtered, filter cake removed, and dried in vacuo to provide N-hydroxy-2(R)-[(4-methoxybenzenesulfonyl)(4-picolyl)amino]-2-(transpropoxycyclohexyl)-acetamide hydrochloride as a white solid, m.p. 135°–140° C., of the formula

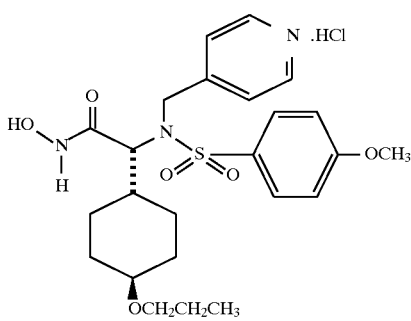

The starting material is prepared as follows:

D-4-hydroxyphenylglycine (10 g) is dissolved in 3 N sodium hydroxide (20 ml). Water (180 ml) and then Raney nickel (27 g) are added. The reaction mixture is hydrogenated at about 3 atmospheric pressure and 50°–80° C. overnight The reaction mixture is filtered through Celite and reduced in volume to about 85 ml and dioxane (85 ml) is added The solution of 4-hydroxycyclohexylglycine (see Con. Czech. Chem. Comm. 49, 712–742 (1984)) is cooled to 0° C. and treated with triethylamine (11.37 ml) and 4-methoxybenzenesulfonyl chloride (10.95 g). The reaction mixture is allowed to warm to room temperature and stirred over the weekend. The dioxane is removed in vacuo and the remaining aqueous solution is diluted with 1 N hydrochloride acid. The resulting precipitate is collected, washed with water and ether to yield (R)-N-(4-methoxybenzenesulfonyl) 4hydroxycyclohexylglycine. A mixture of crude (R)-N-(4-methoxybenzenesulfonyl)-4-hydroxycyclohexylglycine (7.0 g, 20.4 mmol) in dimethylformamide (100 mL) containing N,N-dicyclohexylamine (3.7 g, 20.4 mmol) and benzyl bromide (3.5 g, 20.4 mmol) is stored at room temperature for 24 hours. The mixture is diluted with water and extracted with ethyl acetate. The combined organic extracts are washed with brine, dired ($Na_2SO_4$), filtered, and concentrated in vacuo to yield (R)-N-(4-methoxybenzenesulfonyl)-4-hydroxycyclohexylglycine benzyl ester as a mixture of diastereomers.

To a solution of crude (R)-N-(4-methoxybenzenesulfonyl)-4-hydroxycyclohexylglycine benzyl ester (8.67 g, 20 mmol) in dichloromethane (66 mL) at 0° C. is added a solution of sodium bromide (2.06 g, 20 mmol) in water (10 mL) dropwise followed by addition of 2,2,6,6-tetramethyl-1-piperidinyloxy free radical (IEMPO, 27 mg). To this mixture is added dropwise an aqueous solution of 5% sodium hypochlorite (34.2 mL, 34.3 mmol, Clorox brand) and water (34.2 mL) in which the pH is adjusted to 8.6 with sodium bicarbonate before addition. Addition time of the resulting pH adjusted aqueous sodium hypochlorite solution is 30 minutes and stirring is continued for another 20 minutes while maintaining a reaction temperate of 0° C. The dichloromethane layer is separated and successively washed with 10% aqueous potassium hydrogen sulfate (40 mL), a small amount of 10% aqueous potassium iodide (3×30 mL), 10% aqueous sodium thiosulfate (60 mL), and brine (40 mL). The organic layer is dried ($MgSO_4$), filtered, and concentrated in vacuo to provide solid which could be further purified by recrystallization from ethyl acetate to furnish (R)-N-(4-methoxybenzenesulfonyl)-4-oxocyclohexylglycine benzyl ester.

To a mixture of (R)-N-(4-methoxybenzenesulfonyl)4-oxocyclohexylglycine benzyl ester (15 g, 34.6 mmol) in n-propanol (7 mL, 93.2 mmol) containing phenylsilane (5.2 mL, 43.3 mmol) is added dropwise trifluoroacetic acid and the mixture is stirred at room temperature overnight. The mixture is diluted with ethyl acetate and washed with saturated aqueous sodium bicarbonate. The organic layer is dried ($MgSO_4$), filtered, and concentrated in vacuo. The crude product is purified by silica gel chromatography (1% to 5% ethyl acetate/methylene chloride) to provide (R)-N-(4-methoxybenzenesulfonyl)-cis-4-propoxycyclohexylglycine benzyl ester and (R)-N-(4-methoxybenzensulfonyl)-trans-4-propoxycyclohexylglycine benzyl ester.

To a solution of (R)-N-(4-methoxybenzenesulfonyl)-trans-4-propoxycyclohexylglycine benzyl ester (4.0 g, 8.42 mmol) in dimethylformamide (55 mL) is added 4-picolyl chloride hydrochloride (1.5 g, 8.95 mmol) followed by potassium carbonate (11.6 g, 84.2 mmol). The reaction mixture is stirred at room temperature overnight. The mixture is then diluted with water and extracted with ethyl acetate. The combined organic extracts are washed with brine, dried ($Na_2SO_4$) and the solvent is evaporated to give benzyl 2(R)-[(4-methoxybenzenesulfonyl)(4-picolyl)amino]-2-(trans-4-propoxycyclohexyl)-acetate as a crude product.

A solution of benzyl 2(R)-[(4-methoxybenzenesulfonyl)(4-picolyl)amino]-2-(trans-4-propoxycyclohexyl)-acetate (3.0 g, 5 mmol) in ethanol (50 mL) containing 3 N hydrochloric acid (5 mL, 15 mmol) is hydrogenated at 50 psi in the presence of 5% palladium on charcoal (200 mg) at room temperature for 4 hours. The reaction mixture is filtered through celite washing with ethanol and concentrated in vacuo to provide 2(R)-[(4-methoxybenzenesulfonyl)(4-picolyl)amino]-2-(trans-4-propoxycyclohexyl) acetic acid hydrochloride as a crude product.

2(R)-[(4-methoxybenzenesulfonyl)(4-picolyl)amino]-2-(trans-4-propoxycyclohexyl) acetic acid hydrochloride (2.65 g, 4.82 mmol), 1-hydroxybenzotriazole (0.65 g, 4.81 mmol), 4-methylmorpholine (2.93 mL, 26.5 mmol), and O-t-butylhydroxylamine hydrochloride (1.81 g, 14.4 mmol) are dissolved in methylene chloride (100 mL). N-[dimethylaminopropyl]-N'-ethylcarbodiimide hydrochloride (1.1 g, 5.8 mmol) is added, and the reaction is stirred overnight. The reaction is then diluted with water and extracted with methylene chloride. The combined organic extracts are washed with brine, dried ($Na_2SO_4$), and the solvent is evaporated. The crude product is purified by silica gel chromatography (5% methanoilmethylene chloride) to give N-(t-butyloxy)-2(R)-[(4-methoxybenzenesulfonyl)-(4-picolyl)amino]-2-(trans-4-propoxy-cyclohexyl)-acetamide.

EXAMPLE 2

The following compounds are prepared similarly to example 1:

(a) N-hydroxy-2(R)-[(4-methoxybenzenesulfonyl)(4-picolyl)amino]-2-(trans-4-methoxycyclohexyl)-acetamide hydrochloride, m.p. 145°–155° C.

(b) N-hydroxy-2(R)-[(4-methoxybenzenesulfonyl)(4-picolyl)amino]-2-(trans-4-ethoxycyclohexyl)-acetamide hydrochloride, m.p. 128°–135° C.

(c) N-hydroxy-2(R)-[(4-methoxybenzenesulfonyl)(4-picolyl)amino]-2-(trans-4-butoxy-cyclohexyl)-acetamide hydrochloride, m.p. 132°–137° C.

(d) N-hydroxy-2(R)-[(4-methoxybenzenesulfonyl)(4-picolyl)amino]-2-(trans-4-pentoxy-cyclohexyl)-acetamide hydrochloride, m.p. 135°–145° C.

(e) N-hydroxy-2(R)-[(4-methoxybenzenesulfonyl)(4-picolyl)amino]-2-[trans-4-(2-phenethyloxy)cyclohexyl]-acetamide hydrochloride, m.p. 120°–130° C.

(f) N-hydroxy-2(R)-[(4-methoxybenzenesulfonyl)(4-picolyl)amino]-2-[trans-4-(2-(1-naphthyl)-ethoxy)cyclohexyl]-acetamide hydrochloride, m.p. 125°–145° C.

(g) N-hydroxy-2(R)-[(4-methoxybenzenesulfonyl)(4-picolyl)amino]-2-(trans-4-isopropoxycyclohexyl)acetamide hydrochloride, m.p. 140°–145° C.

(h) N-hydroxy-2(R)-[(4-methoxybenzenesulfonyl)(4-picolyl)amino]-2-(trans-4-isobutoxy-cyclohexyl)acetamide hydrochloride, m.p. 126°–134° C.

(i) N-hydroxy-2(R)-[(4-methoxybenzenesulfonyl)(4-picolyl)amino]-2-(trans-4-cyclohexyloxycyclohoxyl)-acetamide hydrochloride, m.p. 135°–144° C.

(j) N-hydroxy-2(R)-[(4-methoxybenzenesulfonyl)(4-picolyl)amino]-2-trans-4-(2-methoxyethoxy)cyclohexyl]-acetamide hydrochloride, m.p. 108°–117° C.

(k) N-hydroxy-2(R)-[(4-methoxybenzonesulfonyl)(4-picolyl)amino]-2-[trans-4-(2-fluoroethoxy)cyclohexyl]-acetamide hydrochloride, m.p. 130°–141° C.

(1) N-hydroxy-2(R)-[(4-methoxybenzenesulfonyl)(4-picolyl)amino]-2-(trans-4-neopentoxycyclohexyl)-acetamide hydrochloride, m.p. 125°–134° C.

(m) N-hydroxy-2(R)-[(4-methoxybenzenesulfonyl)(4-picolyl)amino]-2-(cis-4-methoxycyclohexyl)-acetamide hydrochloride, m.p. 142°–149° C.

(n) N-hydroxy-2(R)-[(4-methoxybenzenesulfonyl)(3-picolyl)amino]-2-(trans-4-ethoxycyclohexyl)-acetamide hydrochloride.

(o) N-hydroxy-2(R)-[(4-benzenesulfonyl)(4-picolyl)amino]-2-(trans-4-methoxycyclohexyl)-acetamide trifluoroacetate, m.p. 160°–165° C.

(p) N-hydroxy-2(R)-[(4-ethoxybenzenesulfonyl)(4-picolyl)amino]-2-(trans-4-methoxycyclohexyl)acetamide hydrochloride, m.p. 131° C.

(q) N-hydroxy-2(R)-[(4-propoxybenzenesulfonyl)(4-picolyl)amino]-2-(trans-4-propoxycyclohexyl)-acetamide hydrochloride, m.p. 163°–165° C.

(r) N-hydroxy-2(R)-[(4-butoxybenzenesulfonyl)(4-picolyl)amino]-2-(trans-4-propoxycyclohexyl)-acetamide hydrochloride, m.p. 163°–165° C.

(s) N-hydroxy-2(R)-[(3,4-dimethoxybenzenesulfonyl)(4-picolyl)amino] -2-(trans-4-methoxycyclohexyl)-acetamide hydrochloride, m.p. 164° C.

(t) N-hydroxy-2(R)-((4-methoxybenzenesulfonyl)[2-(4-pyridyl)ethyllamino]-2-(trans-4-ethoxycyclohexyl)-acetamide.

(u) N-hydroxy-2(R)-[(4ethoxybenzenesulfonyl)(4-picolyl)amino]-2-(trans-4-propoxycyclohexyl)acetamide hydrochloride, m.p. 131° C.

(v) N-hydroxy-2(R)-[(4-isobutoxybenzenesulfonyl)(4picolyl)amino]-2-(trans-propoxycyclohexyl)-acetamide hydrochloride, m.p. 145°–146° C.

(w) N-hydroxy-2(R)-[(4-ethoxybenzenesulfonyl)(4-picolyl)amino]-2-(trans-4-ethoxycyclohexyl)-acetamide hydrochloride, m.p. 150°–155° C.

(x) N-hydroxy-2(R)-[(4-ethoxybenzenesulfonyl)(4-picolyl)amino]-2-(trans-4-isobutoxycyclohexyl)acetamide hydrochloride, m.p. 168°–169° C.

(y) N-hydroxy-2(S)-[(4-methoxybenzenesulfonyl)(4-picolyl)amino]-2-(trans4-propoxycyclohexyl)-acetamide trifluoroacetate, m.p. 165°–174° C.

(z) N-hydroxy-2(R)-[(4-ethoxybenzenesulfonyl)(4-picolyl)amino]-2-(cis-4-propoxycyclohexyl)-acetamide hydrochloride, m.p. 131°–133° C.

EXAMPLE 3

(a) To a solution of N-(triphenylmethoxy)-2(R)-[(4-methoxybenzenesulfonyl)(4-picolyl)-amino]-2-(trans-4-methoxy-4-methylcyclohexyl) acetamide (348 mg, 0.48 mmol) in methylene chloride at 0° C. containing triethylsilane (260 pL, 1.63 mmol) is added trifluoroacetic acid (260 pl, 3.4 mmol) dropwise. After 20 minutes, the reaction mixture is directly concentrated in vacuo and diluted with methylene chloride (4 mL). The resulting solution is cooled to 0° C. and acidified with hydrogen chloride gas. The solvent is again removed in vacuo and the residue redissolved with methylene chloride. The solution is triturated by addition of pentane to precipitate out product. The supernatent is removed and the process repeated until all triphenylmethane is removed. The remaining solid precipitate is N-hydroxy-2(R)-[(4-methoxybenzenesulfonyl)(4-picolyl)amino]-2-(trans-4-methoxy-4-mothylcyclohexyl)-acetamide hydrochloride, m.p. 133° C.

The starting material is prepared as follows:

A solution of (R)N-(4-methoxybenzenesulfonyl)-4-oxocyclohexylglycine benzyl ester (see example 1, 5.0 g, 11.6 mmol), in methylene chloride (35 mL) at room temperature is added to a solution of titanium tetrachloride (1.0 M in methylene chloride) (21.2 mL, 21.2 mmol) and dimethyl zinc (1.0 M in heptane) (23.0 mL, 23.0 mmol) at −78° C. in dichloromethane (20 mL). The reaction mixture is stirred at −78° C. for 30 minutes, then warmed slowly to room temperature over 2.5 hours. The reaction mixture is poured into water (700 mL) and extracted with chloroform. The combined organic extracts are washed with water, dried (MgSO$_4$), filtered, and concentrated in vacuo. The crude product is purified by silica gel chromatography (40%, ethyl acetateiexanes) to provide (R)-N-(4-methoxybenzenesulfonyl)-trans-hydroxy-4-methylcyclohexyl glycine benzyl ester and (R)-N-(4-methoxybenzenesulfonyl)-cis-4-methyl-4-hydroxycyclohexylglycine benzyl ester.

To a solution of (R)-N-(4-methoxybenzenesulfonyl)-trans-4-hydroxy-4-methylcyclohexyl glycine benzyl ester (600.0 mg, 1.34 mmol) in methylene chloride (15 mL) containing 2,6-di-tert-butylpyridine (755 I, 3.36 mmol) is added methyl trifluoromethanesulfonate (305 µL, 2.68 mmol) dropwise at room temperature. The reaction mixture is stirred at room temperature overnight then quenched with a small amount of methanol. The mixture is diluted with chloroform, then washed with saturated aqueous ammonium chloride and water. The organic layer is dried (MgSO$_4$), filtered, and concentrated in vacuo. The crude product is purified by silica gel chromatography (35% ethyl acetate/hexanes) to provide (R)-N-(4-methoxybenzenesulfonyl)-trans 4-methoxy-4-methylcyclohexylglycine benzyl ester.

Hydrogenolysis of the benzyl ester to the acid and treatment with O-tritylhydroxylamine (instead of O-t-butylhydroxylamine) as in example 1 yields N-(triphenylmethoxy)-2(R)-[(4-methoxybenzenesulfonyl)(4-picolyl)amino] 2-(trans-4-methoxy-4-methylcyclohexyl) acetamide.

(b) Similarly prepared is N-hydroxy-2(R)-[4-methoxybenzenesulfonyl)(4-picolyl)-amino]-2-(cis-4-methoxymethyl-cyclohexyl)-acetamide hydrochloride m.p. 128° C.

EXAMPLE 4

Preparation of 3000 capsules each containing 25 mg of the active ingredient, for example, N-hydroxy-2(R)-[(4- methoxybenzenesulfonyl)(4-picolyl)amino]-2-(transpropoxycyclohexyl)-acetamide:

| Active ingredient | 75.00 g |
|---|---|
| Lactose | 750.00 g |
| Avicel PH 102 (microcrystalline cellulose) | 300.00 g |
| Polyplasdone XL (polyvinylpyrrolidone) | 30.00 g |
| Purified water | q.s. |
| Magnesium stearate | 9.00 g |

The active ingredient is passed through a No. 30 hand screen.

The active ingredient, lactose, Avicel PH 102 and Polyplasdone XL are blended for 15 minutes in a mixer. The blend is granulated with sufficient water (about 500 mL), dried in an oven at 35° C. overnight, and passed through a No. 20 screen.

Magnesium stearate is passed through a No. 20 screen, added to the granulation mixture, and the mixture is blended for 5 minutes in a mixer. The blend is encapsulated in No. 0 hard gelatin capsules each containing an amount of the blend equivalent to 25 mg of the active ingredient.

What is claimed is:

1. A compound of the formula I

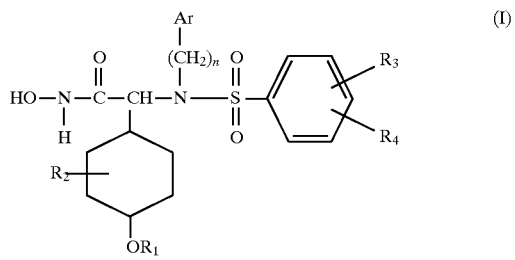

wherein

Ar represents carbocyclic aryl, heterocyclic aryl or biaryl;

$R_1$ represents lower alkyl, cycloalkyl, (carbocyclic or heterocyclic aryl)-lower alkyl, lower alkoxy-lower alkyl, carbocyclic aryl, heterocyclic aryl, cycloalkyl-lower alkyl or halogen-lower alkyl;

$R_2$ represents hydrogen or lower alkyl;

$R_3$ and $R_4$ represent independently hydrogen, lower alkyl, lower alkoxy, halogen, hydroxy, acyloxy, lower alkoxy-lower alkoxy, trifluoromethyl or cyano; or $R_3$ and $R_4$ together on adjacent carbon atoms represent lower alkylenedioxy;

n represents an integer from 1 to 5;

a pharmaceutically acceptable prodrug derivative thereof; or a pharmaceutically acceptable salt thereof.

2. A compound according to claim 1 of the formula II

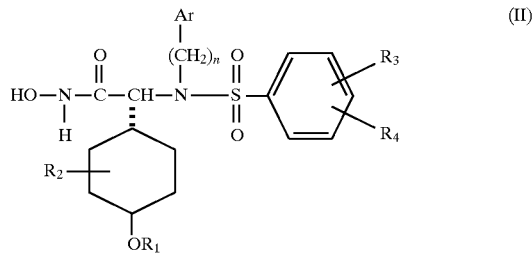

in which the configuration of the asymmetric carbon atom of the α-aminohydroxamic acid moiety to which is attached the cyclohexane ring is assigned the (R)-configuration and wherein Ar, n, $R_1$, $R_2$, $R_3$ and $R_4$ have meaning as defined in said claim, a pharmaceutically acceptable prodrug derivative thereof; or a pharmaceutically acceptable salt thereof.

3. A compound according to claim 1 of the formula III

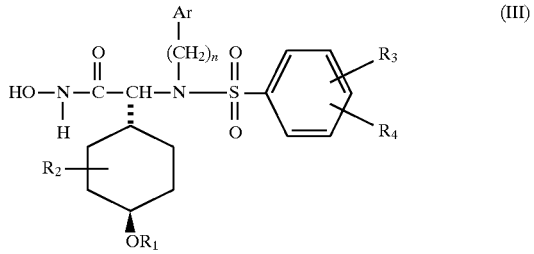

wherein

Ar represents carbocyclic or heterocyclic aryl;

$R_1$ represents lower alkyl, cycloalkyl, (carbocyclic or heterocyclic aryl)-lower alkyl or lower alkoxy-lower alkyl;

$R_2$ represents hydrogen or lower alkyl;

$R_3$ is hydrogen, lower alkoxy or halogen;

$R_4$ is hydrogen or lower alkoxy; or $R_3$ and $R_4$ together on adjacent carbon atoms represent methylenedioxy; and n is 14;

a pharmaceutically acceptable prodrug derivative thereof; or a pharmaceutically acceptable salt thereof.

4. A compound according to claim 3 of formula IIII wherein Ar represents heterocyclic aryl selected from pyridyl, quinolinyl, pyrrolyl, thiazolyl, isoxazolyl, triazolyl, tetrazolyl, pyrazolyl, imidazolyl, thienyl, and any said radical mono- or di-substituted by lower alkyl or halogen; $R_1$ represents lower alkyl; cycloalkyl or lower alkoxy-lower alkyl; $R_2$ represents hydrogen or lower alkyl; $R_3$ and $R_4$ represent hydrogen or lower alkoxy; and n is 1–4; a pharmaceutically acceptable prodrug derivative thereof; or a pharmaceutically acceptable salt thereof.

5. A compound according to claim 3 of formula IIII wherein $R_3$ is at the para position and $R_4$ is at the meta position.

6. A compound according to claim 3 of formula IIII wherein Ar is heterocyclic aryl selected from pyridyl, quinolinyl, pyrrolyl, thiazolyl, isoxazolyl, triazolyl, tetrazolyl, pyrazolyl, imidazolyl, thienyl, and any said radical mono- or di-substituted by lower alkyl or halogen; $R_1$ is lower alkyl; $R_2$ is hydrogen; $R_3$ is para-lower alkoxy; $R_4$ is hydrogen; and n is 1 or 2; or a pharmaceutically acceptable salt thereof.

7. A compound according to claim 3 wherein Ar is pyridyl.

8. A compound according to claim 3 of formula m wherein Ar is pyridyl; $R_1$ is lower alkyl; $R_2$ and $R_4$ are hydrogen; $R_3$ is para-lower alkoxy; and n is 1; or a pharmaceutically acceptable salt thereof.

9. A compound according to claim 8 wherein Ar is 3- or 4-pyridyl.

10. A compound according to claim 8 of formula m wherein Ar is 3- or 4-pyridyl; $R_1$ is straight chain $C_2$–$C_5$-alkyl; $R_2$ and $R_4$ are hydrogen; $R_3$ is para-lower alkoxy; and n is 1; or a pharmaceutically acceptable salt thereof.

11. A compound according to claim 8 wherein Ar is 4-pyridyl.

12. A compound according to claim 10 wherein Ar is 4-pyridyl.

13. A compound according to claim 8 of formula HI wherein Ar is 4-pyridyl; $R_1$ is $C_2$–$C_4$alkyl; $R_2$ and $R_4$ are hydrogen; $R_3$ is para-ethoxy; and n is 1; or a pharmaceutically acceptable salt thereof.

14. A compound according to claim 8 which is N-hydroxy-2(R)-[(4-methoxybenzenesulfonyl)(4-picolyl) amino]-2-(trans-4-propoxycyclohexyl)-acetamide, or a pharmaceutically acceptable salt thereof.

15. A compound according to claim 8 which is N-hydroxy-2(R)-[(4-ethoxybenzenesulfonyl)(4-picolyl) amino]-2-(trans-4-propoxycyclohexyl)acetamide, or a pharmaceutically acceptable salt thereof.

16. A compound according to claim 8 which is N-hydroxy-2(R)-[(4-ethoxybenzenesulfonyl)(4-picolyl) amino]-2-(trans-4-ethoxycyclohexyl)-acetamide, or a pharmaceutically acceptable salt thereof.

17. A compound according to claim 8 which is N-hydroxy-2-(R)-[(4-ethoxybenzenesulfonyl)(4-picolyl) amino]-2-(trans-4-isobutoxycyclohexyl)-acetamide, or a pharmaceutically acceptable salt thereof.

18. A pharmaceutical composition comprising an effective TNF-alpha convertase inhibiting amount of a compound of claim 1 in combination with one or more pharmaceutically acceptable carriers.

19. A method of treating TNF-alpha dependent conditions in mammals which comprises administering to a mammal in need thereof an effective TNF-alpha convertase inhibiting amount of a compound of claim 1.

20. A method of treating inflammation, arhritis, or tumors in mammals which comprises administering to a mammal in need thereof a correspondingly effective amount of a compound of claim 1.

21. A method of inhibiting TNF-α activity in mammals which comprises administering to a mammal in need thereof an effective TNF-α convertase inhibiting amount of a compound of claim 15.

22. A method of treating arthritis in mammals which comprises administering to a mammal in need thereof a therapeutically effective amount of a compound of claim 15.

23. A process for the preparation of a compound of formula I according to claim 1, which comprises condensing a carboxylic acid of formula IV

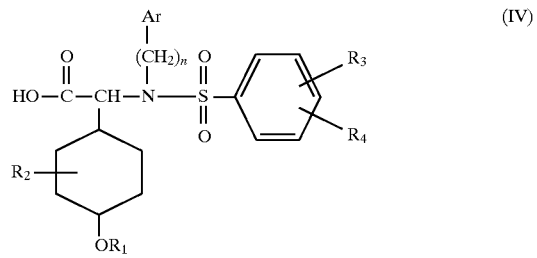

or a reactive functional derivative thereof, wherein Ar, n and $R_1$–$R_4$ having meaning as defined hereinabove, with hydroxylamine of formula V,

$NH_2$—OH          (V)

optionally in protected form, or a salt thereof;

and, if necessary, temporarily protecting any interfering reactive group(s), and then liberating the resulting compound of the invention; and, if required or desired, converting a resulting compound of the invention into another compound of the invention, and/or, if desired, converting a resulting free compound into a salt or a resulting salt into a free compound or into another salt; and/or separating a mixture of isomers or racemates obtained into the single isomers or racemates; and/or, if desired, resolving a racemate into the optical antipodes.

* * * * *